US012564696B2

(12) United States Patent
Eifler

(10) Patent No.: US 12,564,696 B2
(45) Date of Patent: Mar. 3, 2026

(54) HARNESS WITH EYEGLASS REGION

(71) Applicant: Loewenstein Medical Technology S.A., Luxembourg (LU)

(72) Inventor: Martin Eifler, Glueckstadt (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 848 days.

(21) Appl. No.: 17/804,124

(22) Filed: May 26, 2022

(65) Prior Publication Data

US 2022/0379062 A1 Dec. 1, 2022

(30) Foreign Application Priority Data

May 27, 2021 (DE) .......................... 102021002733.7

(51) Int. Cl.
*A61M 16/06* (2006.01)

(52) U.S. Cl.
CPC .... *A61M 16/0683* (2013.01); *A61M 16/0666* (2013.01)

(58) Field of Classification Search
CPC ........................... A41D 13/11; A41D 13/1161; A41D 13/1184; A41D 13/1209; A41D 2200/20; A42B 1/006; A42B 1/0182; A42B 1/02; A42B 1/046; A42B 1/12; A42B 1/16; A42B 1/201; A42B 1/22; A42B 1/24; A42B 1/247; A42B 7/00; A45C 11/04; A45F 2003/002; A45F 2005/006; A45F 5/00; A45F 5/02; A45F 5/1541; A61B 2090/502; A61B 2562/0215; A61B 2562/0217; A61B 5/0022; A61B 5/01; A61B 5/02055; A61B 5/021; A61B 5/02405; A61B 5/029; A61B 5/0533; A61B 5/0537; A61B 5/0816; A61B 5/087; A61B 5/1112; A61B 5/1135; A61B 5/14552; A61B 5/165; A61B 5/24; A61B 5/245; A61B 5/318; A61B 5/369; A61B 5/389; A61B 5/443; A61B 5/4803; A61B 5/4866; A61B 5/6803; A61B 5/7282; A61B 7/00; A61B 90/05; A61F 11/06;

(Continued)

(56) References Cited

U.S. PATENT DOCUMENTS 3,182,658 A * 5/1965 Klinger ................ A62B 18/082 D24/110.2
3,209,755 A * 10/1965 Mccarthy .............. A61M 25/02 351/111

(Continued)

FOREIGN PATENT DOCUMENTS

DE 202020001858 U1 6/2020
GB 1258710 A 12/1971

(Continued)

*Primary Examiner* — Annette Dixon
(74) *Attorney, Agent, or Firm* — Abel Schillinger, LLP

(57) ABSTRACT

A harness for a patient interface comprises, at least in some regions, an eyeglass tunnel which is configured and designed to at least partially receive at least one eyeglass arm. The eyeglass tunnel is in the temple portion of the harness, the temple portion being the portion of the harness which, after being placed on a head of a user, extends over a temple region of the head. The harness preferably comprises an inner fabric strand, a strengthening layer, a cushioning layer and an outer fabric strand.

16 Claims, 10 Drawing Sheets

(58) Field of Classification Search

CPC .. A61F 9/02; A61F 9/025; A61F 9/026; A61F 9/027; A61F 9/029; A61M 16/0666; A61M 16/0683; B63B 22/00; D06F 95/006; D06F 95/008; G02C 11/00; G02C 11/02; G02C 2200/02; G02C 2200/16; G02C 2200/24; G02C 3/003; G02C 3/006; G02C 3/02; G02C 3/04; G02C 5/00; G02C 5/001; G02C 5/14; G02C 5/143; G02C 5/146; G02C 5/22; G02C 5/2209; G16H 40/67; Y10S 2/909; Y10S 24/46; Y10T 24/1371; Y10T 24/1374; Y10T 24/1385; Y10T 24/1397; Y10T 24/318; Y10T 24/38; Y10T 24/3927; Y10T 24/3929; Y10T 24/42; Y10T 24/45052; Y10T 24/45178; Y10T 403/54; Y10T 428/24017

See application file for complete search history.

(56) References Cited

U.S. PATENT DOCUMENTS

| | | | | |
|---|---|---|---|---|
| 3,288,547 | A * | 11/1966 | Klinger | A62B 18/082 |
| | | | | 351/158 |
| 3,856,007 | A * | 12/1974 | Leight | G02C 11/00 |
| | | | | 351/158 |
| 3,988,058 | A * | 10/1976 | Chaney | A42B 1/247 |
| | | | | 2/DIG. 8 |
| 4,836,200 | A | 6/1989 | Clark | |
| 4,843,643 | A * | 7/1989 | Parissenti | A41D 13/1161 |
| | | | | 351/158 |
| 4,930,163 | A * | 6/1990 | King | B63C 11/12 |
| | | | | 351/158 |
| 4,965,887 | A * | 10/1990 | Paoluccio | G02C 11/00 |
| | | | | 2/205 |
| 5,033,128 | A * | 7/1991 | Torres | A62B 18/00 |
| | | | | 2/427 |
| 5,193,534 | A * | 3/1993 | Peppler | A61M 16/0666 |
| | | | | 128/207.18 |
| 5,201,856 | A * | 4/1993 | Edwards | G02C 3/003 |
| | | | | 2/209 |
| 5,339,119 | A * | 8/1994 | Gardner | G02C 11/00 |
| | | | | 351/44 |
| 5,927,279 | A * | 7/1999 | Oviatt | A61F 9/04 |
| | | | | 2/13 |
| 6,302,111 | B1 * | 10/2001 | Bremenstul | A61F 11/12 |
| | | | | 128/866 |
| 7,275,270 | B2 * | 10/2007 | Cotutsca | A42B 1/247 |
| | | | | 2/209.13 |
| 8,382,279 | B2 * | 2/2013 | Phillips | G02C 7/16 |
| | | | | 351/158 |
| 8,387,163 | B2 * | 3/2013 | Beliveau | A41D 13/11 |
| | | | | 128/857 |
| 11,766,080 | B2 * | 9/2023 | Lamoncha | B33Y 10/00 |
| | | | | 2/427 |
| 2004/0025885 | A1 | 2/2004 | Payne | |
| 2005/0061326 | A1 | 3/2005 | Payne | |
| 2006/0081252 | A1 | 4/2006 | Wood | |
| 2007/0056590 | A1 | 3/2007 | Wolfson | |
| 2007/0252946 | A1 | 11/2007 | Welchel et al. | |
| 2008/0047559 | A1 * | 2/2008 | Fiori | A61M 16/0666 |
| | | | | 128/207.18 |
| 2013/0263859 | A1 | 10/2013 | Ho et al. | |
| 2015/0283348 | A1 | 10/2015 | Harp et al. | |
| 2016/0256655 | A1 | 9/2016 | Mah et al. | |
| 2018/0099113 | A1 | 4/2018 | Bell et al. | |
| 2020/0187579 | A1 * | 6/2020 | Babalola | A42B 1/247 |
| 2022/0030974 | A1 * | 2/2022 | Kane | G02C 11/00 |
| 2022/0053864 | A1 * | 2/2022 | Kim | A41D 13/1161 |
| 2024/0058559 | A1 | 2/2024 | Rafiqpoor | |

FOREIGN PATENT DOCUMENTS

| | | | |
|---|---|---|---|
| NO | 850786 L | * | 9/1985 |
| WO | 2012080887 A2 | | 6/2012 |

* cited by examiner

HARNESS WITH EYEGLASS REGION

CROSS-REFERENCE TO RELATED APPLICATIONS

The present application claims priority under 35 U.S.C. § 119 of German Patent Application No. 102021002733.7, filed May 27, 2021, the entire disclosure of which is expressly incorporated by reference herein.

BACKGROUND OF THE INVENTION

1. Field of the Invention

The invention relates to a harness with eyeglass region.

2. Discussion of Background Information

Patient interfaces or respiratory masks are used for ventilation, for respiratory assistance or as a protective mask against aerosols composed of solid or liquid particles.

Respiratory masks for ventilation or respiratory assistance form the interface between a user or patient and a ventilator and have to satisfy strict requirements as regards stability and safety and at the same time must offer sufficient comfort for the user.

Respiratory masks are usually fixed on the head of the user via a harness. The harness can cause problems for users who wear eyeglasses, since wearing eyeglasses together with a respiratory mask is uncomfortable or even impossible.

A distinction is made between respiratory masks with forehead supports and respiratory masks without forehead supports. Respiratory masks with forehead supports make wearing normal eyeglasses almost impossible, since the forehead support blocks the contact surface for eyeglasses. After the respiratory mask has been fitted in place, it is no longer possible for normal eyeglasses to be put on or taken off.

In the case of respiratory masks without forehead supports, it is possible in principle to wear eyeglasses. However, problems may also arise here, since the harness generally extends at least in part over the temples, over which the eyeglass arms also normally extend. Respiratory masks without forehead supports usually have stiffening devices in the harness, in order to ensure sufficient stability and a good fit of the respiratory mask. The stiffened region is generally cushioned in the direction of the face, in order to increase the wearing comfort.

The user could try wearing the eyeglasses over the harness. However, this can cause the eyeglasses to deform or bend and not sit correctly. If the user pushes the eyeglasses under the harness, unpleasant pressure may arise, since the eyeglass arms are pressed against the face by the harness. This problem prevents comfortable wearing of the eyeglasses, particularly over a long period of time. Moreover, wearing the eyeglasses with the eyeglass arms extending under the harness can have a negative impact on the fit of the respiratory mask and cause leakage.

There is therefore a need for respiratory masks which have a harness and which permit simultaneous use of eyeglasses without damaging the latter and while at the same time ensuring a stable, secure and comfortable fit of the respiratory mask.

SUMMARY OF THE INVENTION

The invention provides a harness for a patient interface. According to the invention, the harness has, at least in some regions, an eyeglass tunnel which is configured and designed to at least partially receive at least one eyeglass arm.

In some embodiments, the harness is characterized in that the harness comprises a temple portion, which at least in some regions has the eyeglass tunnel, wherein the temple portion is the portion of the harness which, after being placed on a head of a user, extends over a temple region of the head.

In some embodiments, the harness is characterized in that the harness comprises an inner substance strand and/or a strengthening layer and/or a cushioning layer and/or an outer substance strand.

In some embodiments, the harness is characterized in that the eyeglass tunnel is reversible and/or irreversible.

In some embodiments, the harness is characterized in that the reversible eyeglass tunnel is formed by the action of the eyeglass arm and/or by a releasable add-on to the harness.

In some embodiments, the harness is characterized in that the irreversible eyeglass tunnel is formed by a non-releasable add-on to the harness and/or by an at least partial cutout in the inner substance strand and/or in the strengthening layer and/or in the cushioning layer and/or in the outer substance strand and/or by an at least partial pre-shaping, at least in some regions, of the harness.

In some embodiments, the harness is characterized in that a material weakening is formed at least in some regions in the cushioning layer and/or in the strengthening layer and/or in the substance strand of the temple portion.

In some embodiments, the harness is characterized in that the weakening is designed and configured in such a way that the eyeglass tunnel is formed reversibly at least in some regions in the temple portion by the action of the eyeglass arm.

In some embodiments, the harness is characterized in that the weakening is formed by an at least regionally lower degree of hardness of the material of the cushioning layer and/or of the strengthening layer and/or of the substance strand.

In some embodiments, the harness is characterized in that the cushioning layer has a thickness, which is constant, or which in at least some regions is not constant.

In some embodiments, the harness is characterized in that the cushioning layer has a substantially constant thickness and in the temple portion has a thickness which is at least regionally greater than the thickness of the cushioning layer.

In some embodiments, the harness is characterized in that the material of the cushioning layer is displaced by the action of the eyeglass arm in such a way that the eyeglass tunnel is reversible.

In some embodiments, the harness is characterized in that the harness comprises at least one spacer cushion.

In some embodiments, the harness is characterized in that the spacer cushion is connected at least in some regions to the harness, preferably at least in some regions to the temple portion.

In some embodiments, the harness is characterized in that the spacer cushion is connected releasably and/or non-releasably to the harness.

In some embodiments, the harness is characterized in that the spacer cushion is fastened to the harness and/or is integrated in the harness.

In some embodiments, the harness is characterized in that the spacer cushion is arranged in the temple portion in such a way that the eyeglass tunnel is formed reversibly and/or irreversibly.

In some embodiments, the harness is characterized in that the eyeglass tunnel is formed by an at least partial cutout in the cushioning layer and/or in the strengthening layer and/or in the substance strand.

In some embodiments, the harness is characterized in that the eyeglass tunnel is formed by an at least partial cutout of the cushioning layer and/or of the strengthening layer and/or of the substance strand.

In some embodiments, the harness is characterized in that the temple portion has a length L, and the cutout in the cushioning layer and/or in the strengthening layer and/or in the substance strand and/or the cutout of the cushioning layer and/or of the strengthening layer and/or of the substance strand comprises from about 20% to about 100% of the length L of the temple portion, preferably from about 50% to about 100%, particularly preferably about 80% of the length L of the temple portion.

In some embodiments, the harness is characterized in that the harness has, at least in some regions, an at least partial pre-shaped contour which irreversibly forms the eyeglass tunnel.

In some embodiments, the harness is characterized in that the inner substance strand and/or the cushioning layer and/or the strengthening layer and/or the outer substance strand have a pre-shaped contour in the temple portion.

In some embodiments, the harness is characterized in that the harness is pre-shaped in the temple portion in such a way that the harness, after being placed on the head of a user, is at least partially spaced apart from the head of the user, so that the eyeglass tunnel is formed.

In some embodiments, the harness is characterized in that the inner substance strand and the cushioning layer do not have a pre-shaped contour in the temple portion, and the strengthening layer and/or the outer substance strand do have a pre-shaped contour, in such a way that cushioning layer and strengthening layer are spaced apart from each other and form the eyeglass tunnel.

In some embodiments, the harness is characterized in that the eyeglass tunnel is from about 3 mm to about 30 mm high, preferably from about 5 mm to about 20 mm high.

In some embodiments, the harness is characterized in that the eyeglass tunnel, by means of the pre-shaped contour, is from about 3 mm to about 30 mm high, preferably from about 5 mm to about 20 mm high.

BRIEF DESCRIPTION OF THE DRAWINGS

Illustrative embodiments of the harness 10 according to the invention are shown in the drawings, in which.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

A harness 10 according to the invention is shown in the following illustrative embodiments. Further features and advantages of the present invention will become clear from the following descriptions of illustrative embodiments with reference to the figures. The invention is not limited to the illustrative embodiments shown.

Figure 1:
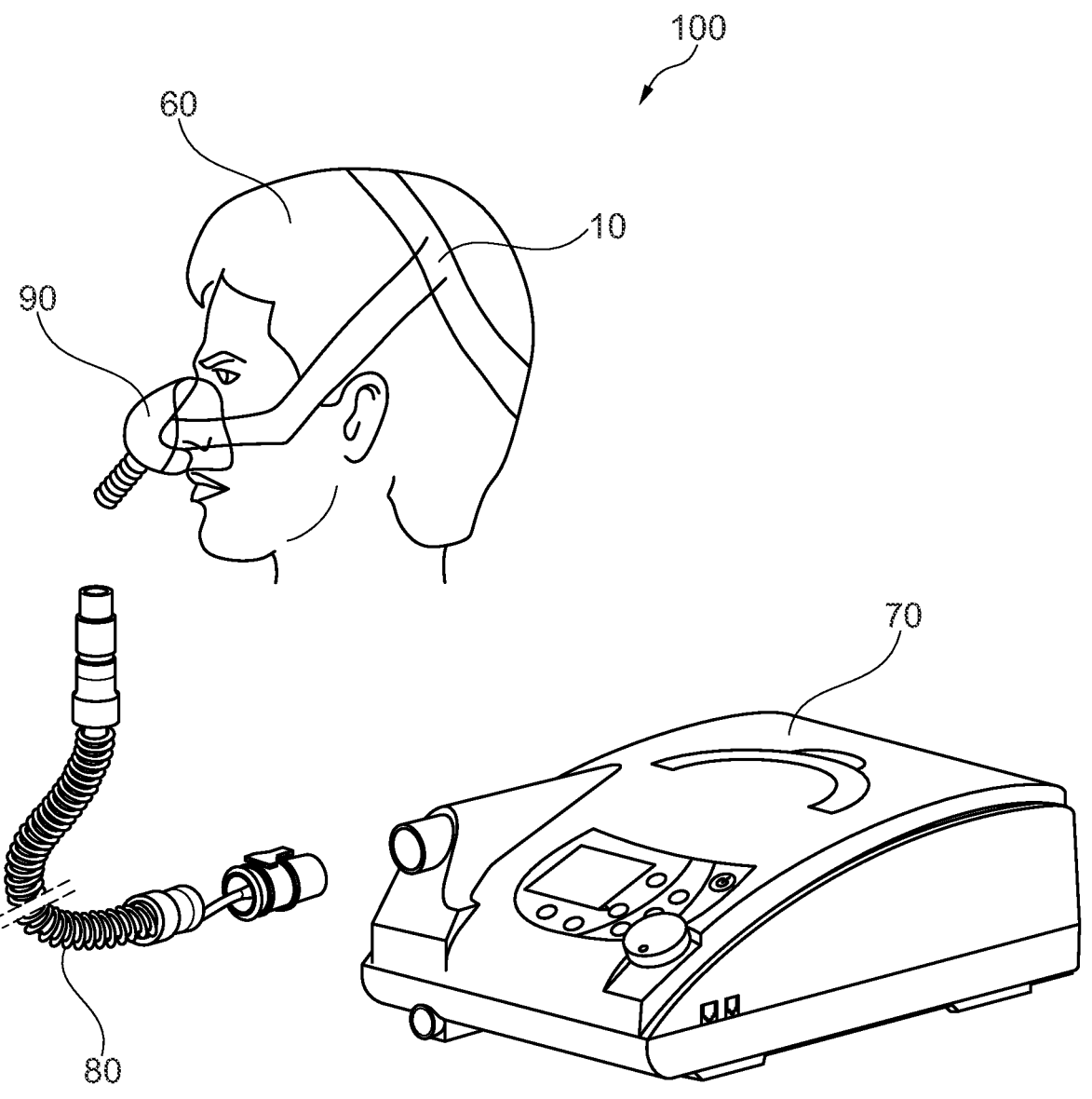
FIG. 1 shows by way of example an overview of a system having a patient interface with harness, which system can be connected to a ventilator in a gas-conducting manner via a line.

The harness 10 according to the invention is suitable for example for use with a system 100 for ventilation, that is to say for use with a patient interface 90 and with a ventilator 70. FIG. 1 shows by way of example an overview of a system 100 having a patient interface 90 with a harness 10, which system can be connected to a ventilator in a gas-conducting manner via a line 80.

A patient interface 90 is understood as any peripheral designed for interaction with a living being. In particular, the patient interface 90 is designed for therapeutic or diagnostic purposes in connection with the ventilator 70. The patient interface 90 can be designed as a respiratory mask. This mask can be a full-face mask, i.e. enclosing the nose and mouth, or a nose mask, i.e. a mask enclosing only the nose. Tracheal tubes or cannulas and so-called nasal cannulas can also be used as patient interface 90. The harness 10 according to the invention is also suitable in particular for nasal pillow masks. Patient interface 90 and respiratory mask are used here as synonyms.

The patient interface 90 can be applied or fastened to the head 60 of a user or patient via a harness 10 according to the invention. User and patient are here used to mean the same thing. When the term user or patient is used, this means any individual using a respiratory mask 90 with a harness 10.

A ventilator 70 is understood to mean all appliances which assist the natural breathing of a user or patient and/or which take over the ventilation of a user or patient and/or which serve for respiratory therapy and/or which act in some other way on the respiration of a user or patient. These include by way of example, but not exclusively, CPAP and BiLevel appliances, anesthesia appliances, respiration therapy appliances, ventilators for use in hospitals, in non-hospital environments or in emergencies, high-flow therapy appliances and coughing machines.

The patient interface 90 and the ventilator 70 are preferably connected to each other via at least one line 80. The line 80 is designed as a gas line, which connects the individual components of the system 100 to one another. The line 80 is preferably flexible and/or rotatable. The line 80 can be designed, for example, as an elastic tube and/or hose and/or hose system.

Patent interface 90, line 80 and ventilator 70 are not shown connected in FIG. 1. A gas-conducting connection can be produced when the line 80 is connected (not shown), e.g., via attachment pieces, at one end to the patient interface 90 and at the other end to the ventilator 70.

Figure 2:
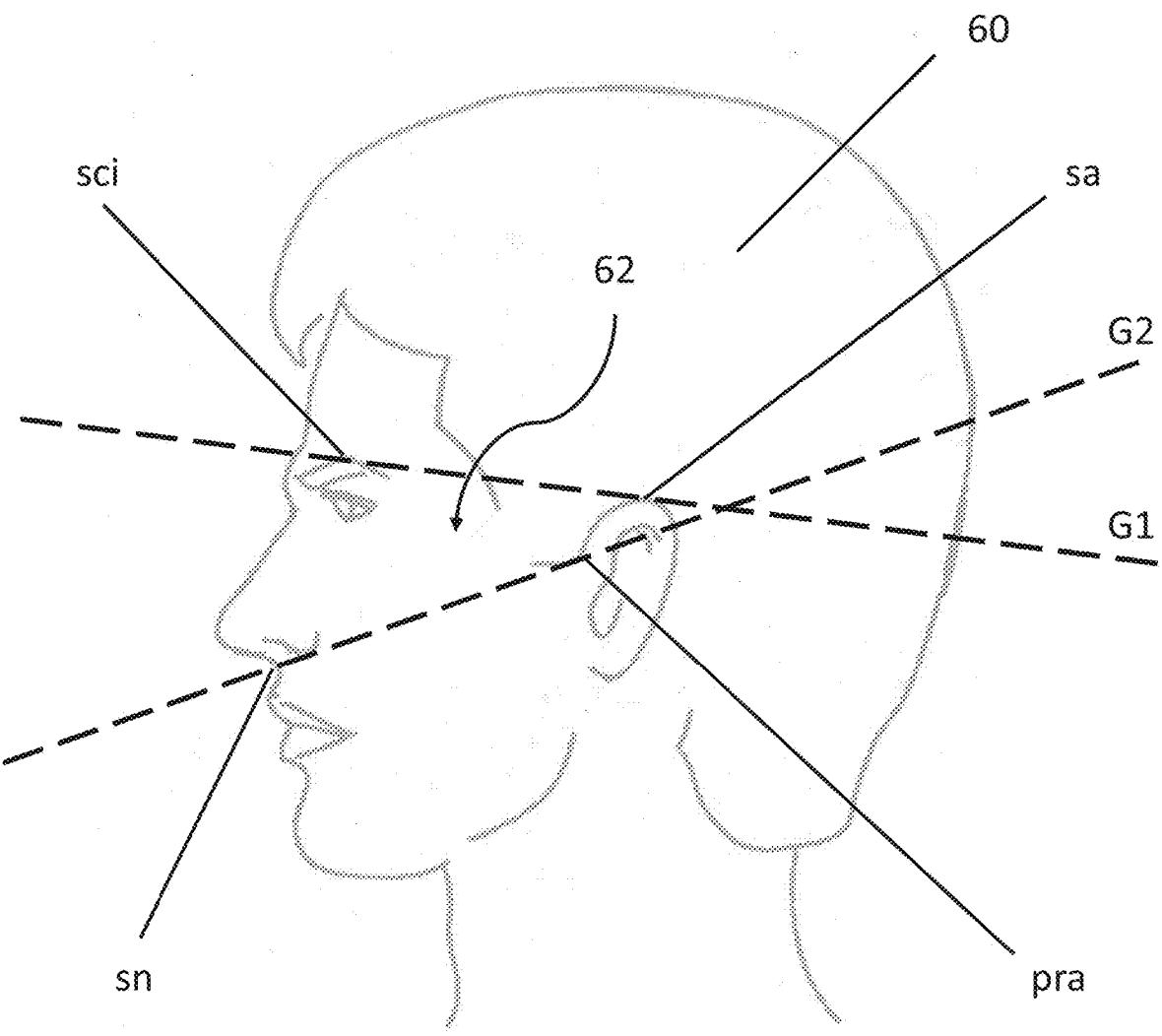
FIG. 2 shows a human head in a side view, illustrating measurement points which are used to define a temple region.

FIG. 2 shows a human head 60 in a side view, illustrating measurement points that are used to define a temple region 62.

For the definition of the regions of the human head 60, reference is here made to the textbook "Anthropologie: Handbuch der vergleichenden Biologie des Menschen" (Fischer Verlag, 4th edition, 1988), the entire disclosure of which is incorporated by reference herein, in which the following measurement points on the head 60 are defined:

| | |
|---|---|
| sa | highest point of the auricle (lat. *Supeaurale*) |
| sci | highest point of the upper margin of the brow (lat. *Superciliare*) |
| pra | point of the base of the ear (lat. *Praeaurale*) |
| sn | subnasal angle (lat. *Subnasale*) |

For the present patent application, the temple region 62 is defined as the region located between two straight lines G1 and G2, where the straight line G1 runs through the measurement points sa and sci, and the straight line G2 runs through the measurement points pra and sn (see FIG. 1). The temple region 62 can deviate by +/−3 cm from the region indicated.

Figure 3A:
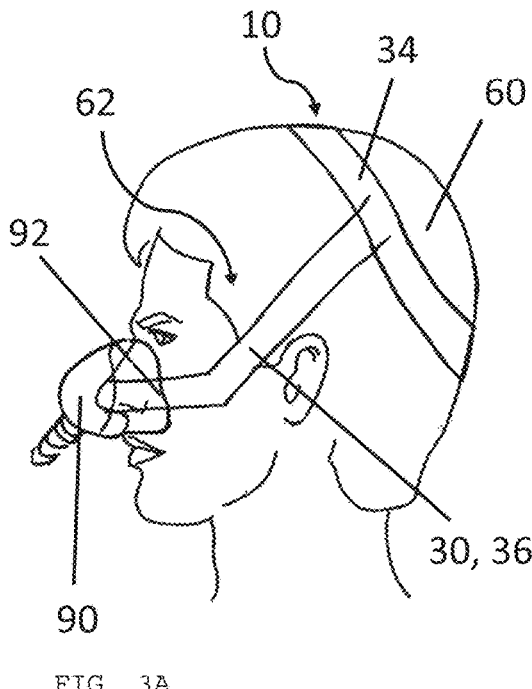
FIGS. 3A to 3D show by way of example how patient interfaces without a forehead support can be fastened to a user's head via a harness according to the invention.
Figure 3B:
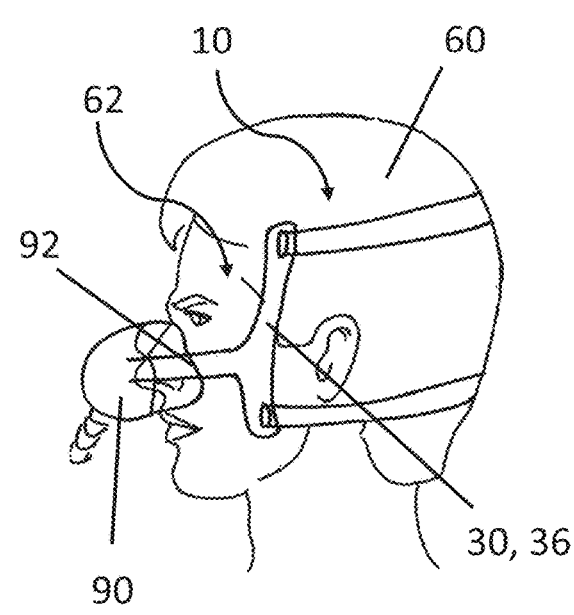
Figure 3C:
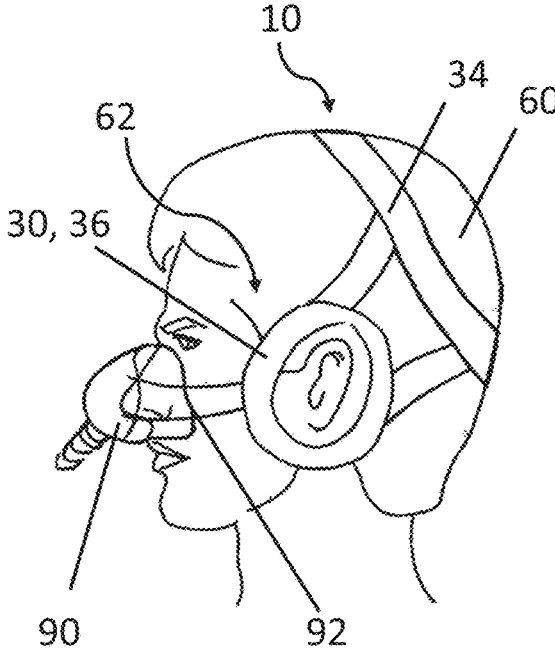
Figure 3D:
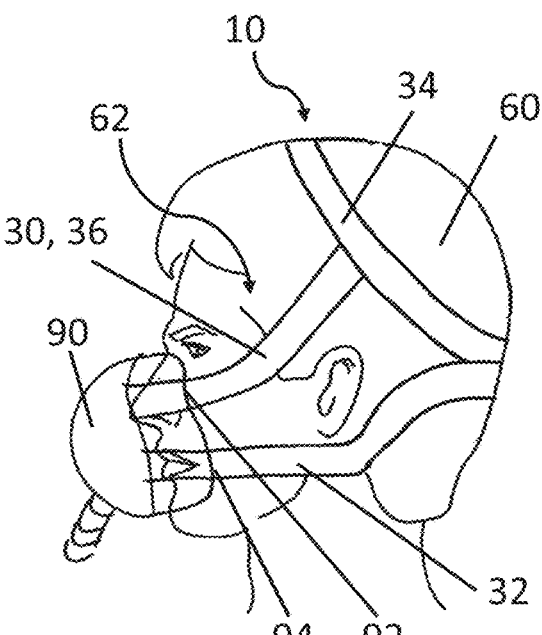

FIGS. 3A-3D show, by way of example, how patient interfaces 90 without forehead supports can be fastened to the head 60 of the user via a harness 10 according to the invention. FIGS. 3A-3C show, by way of example, how, when using a patient interface 90 designed as a nose mask, the harness 10 can be arranged after being placed on the head 60 of the user. FIG. 3D shows, by way of example, how, when using a patient interface 90 designed as a full-face mask, the harness 10 can be arranged after being placed on the head 60 of the user. However, the harness 10 can also extend over other regions of the head 60; the course of the harness 10 is not limited to the examples shown.

The harness 10 according to the invention comprises at least one side portion 30. Patient interfaces 90 designed as nose masks generally include an attachment point 92 for each half of the face. By way of the attachment point 92, the harness 10 can be connected to the patient interface 90. Preferably, the side portion 30 can be connected to the patient interface 90 via the attachment point 92. Several attachment points 92 are also conceivable.

The harness 10 can moreover comprise a base portion 34 (see FIGS. 3A, 3C and 3D). The base portion 34 can be configured and designed to ensure a secure and comfortable fit on the head 60. After being placed on the head, the base portion 34 lies for example in a circular formation around the head 60 and is connected at least to the side portion 30.

Patient interfaces 90 designed as full-face masks preferably include two attachment points 92, 94 for each half of the face (see FIG. 3D). However, it is also possible that full-face masks have only one attachment point 92 or also more than two attachment points 92, 94.

If the patient interface comprises two attachment points 92, 94, as shown in FIG. 3D, the patient interface 90 can be connected to the harness 10 via both attachment points 92, 94. In this way, full-face masks can be fastened to the head 60 of the user in a particularly stable and secure manner.

For this purpose, the harness 10 can comprise a second side portion 32 in addition to the side portion 30. The side portion 30 can preferably be connected to the patient interface 90 via the attachment point 92, and, in addition, the second side portion 32 can be connected to the patient interface 90 via the second attachment point 94. The base portion 34 is for example connected both to the side portion 30 and also to the second side portion 32 (see FIG. 3D).

When the respiratory mask 90 is placed on the head 60 of a user, the harness 10 extends over the head 60 of the user in order to hold the respiratory mask 90 in the desired position.

The side portion 30 generally extends from a first attachment point 92 of the respiratory mask 90 along the cheek and the temple above the ear to the base portion 34. The second side portion 32 generally extends from a second attachment point 94 of the respiratory mask 90 along the lower jaw and below the ear to the base portion 34.

In order to achieve sufficient stability, at least one region of the harness 10, in all known harnesses 10, extends at least in part above the ear. Thus, the harness 10 crosses the temple region 62 generally at least once (see FIGS. 3A-3D).

The temple region 62 is additionally the region over which an eyeglass arm 64 of standard eyeglasses or temple glasses extends (not shown). The eyeglass arm 64 of temple eyeglasses normally extends between the eye region and the upper end of the ear. The eyeglass arm 64 thus extends along and above the temple region 62.

To ensure that a user can use eyeglasses when using a patient interface 90, the region of the harness 10 that extends over the temple is modified according to the invention. The harness 10 thus comprises at least one temple portion 36. The temple portion 36 is designed in such away that the user, despite using a patient interface 90 with a harness 10, is able to put on and take off his or her eyeglasses (not shown).

The temple portion 36 is the portion of the harness 10 which, after the latter is placed on the head 60, extends across the temple region.

This temple portion 36 is usually a region of the side portion 30. However, it is also possible that the temple portion 36 is a portion of the side portion 32 and/or of the base portion 34. The temple portion 36 is arranged within the harness 10 in such a way that, after the harness 10 has been placed on the head 60 of the user, the temple portion 36 at least partially spans the temple region 62.

Figure 4:
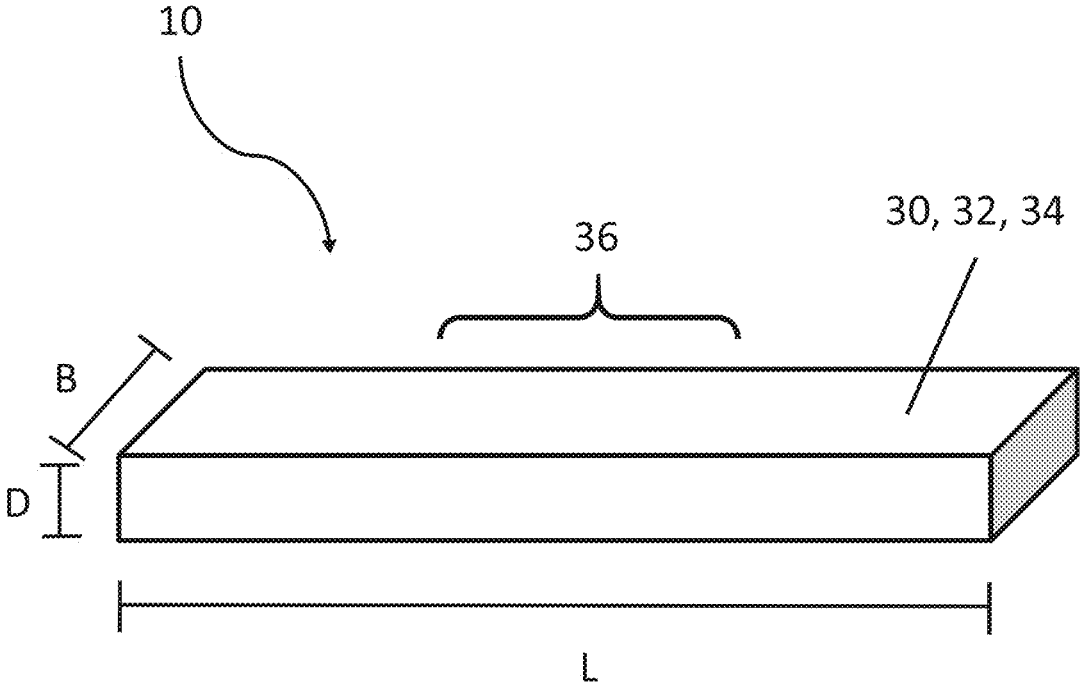
FIG. 4 shows a perspective plan view of a subregion of a side portion or of a second side portion or of a base portion of a harness according to the invention.

FIG. 4 shows a perspective plan view of a subregion of a side portion 30 or of a second side portion 32 or of a base portion 34 of a harness 10 according to the invention.

The harness 10 has a width B, a thickness D and a length L. The width B is usually always greater than the thickness D. The length L is usually greater than the width B.

The illustrated subregion of the harness 10 has the temple portion 36 according to the invention, which temple portion 36 is described in more detail below on the basis of illustrative embodiments with reference to FIGS. 6 to 9.

Figures 5A, 5B, 5C:
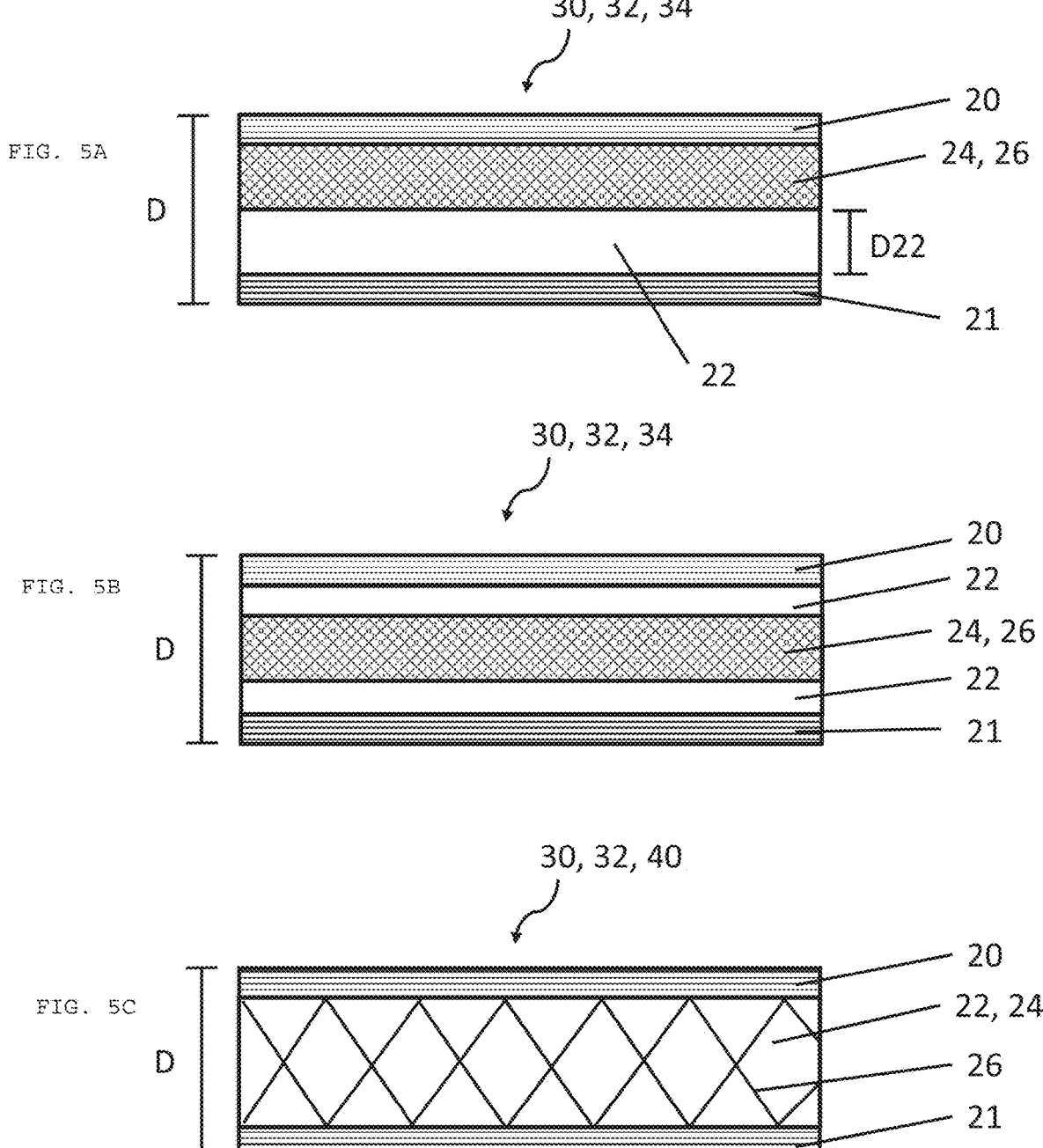
FIGS. 5A to 5C show a cross section through the harness in the region of the side portion or of the second side portion or of the base portion outside the temple portion.

FIGS. 5A to 5C show a cross sections through the harness 10 in the region of the side portion 30 or of the second side portion 32 or of the base portion 34 outside the temple portion 36. FIGS. 5A to 5C illustrate the general structure of a harness 10 for patient interfaces 90 without forehead supports.

The harness 10 comprises at least one strand 21. The strand can be designed, for example, as a substance strand 21. In a simple embodiment (not shown), the harness can comprise only one substance strand 21. In an alternative embodiment, the harness 10 comprises at least two substance strands 20, 21. For example, the harness 10 comprises an outer substance strand 20 and an inner substance strand 21 (FIGS. 5A-5C).

The substance strand facing away from the head 60, when the harness has been placed on the head 60, is referred to herein as the outer substance strand 20. The substance strand facing toward the head 60, when the harness has been placed on the harness 60, is referred to herein as the inner substance strand 21. After placement on the head 60, the inner strand comes into contact at least in part with the facial skin of the user.

Outer substance strand 20 and inner substance strand 21 can be formed in one piece, for example. Outer substance strand 20 and inner substance strand 21 can have a hose-shaped design, for example. Hose-shape means that the outer substance strand 21 and the inner substance strand are connected to each other over the entire length L along the thickness D.

It is also conceivable that outer substance strand 20 and inner substance strand 21 are in two parts. In some embodiments, the outer substance strand 20 and the inner substance strand 21 can be connected to each other at least in some regions. For example, the outer substance strand 20 and the inner substance strand 21 can be adhesively bonded, welded, sewn or connected in a similar fashion to each other at least in some regions.

Outer substance strand 20 and inner substance strand 21 can be produced from the same material. Outer substance strand 20 and inner substance strand 21 can also be produced from different materials.

The substance strand 20, 21 is produced, for example, from a textile such as cotton or silk and/or from synthetic fibers such as polyester, polyurethane, neoprene, spandex and/or nylon. Mixed fabrics are also conceivable. Also conceivable are further substances that appear suitable in respect of biocompatibility, comfort, stability, elasticity and costs.

In some embodiments, the outer substance strand 20 and the inner substance strand 21 are produced from the same material, for example from nylon with polyester and/or from nylon and spandex.

In addition to the at least one substance strand 20, 21, the harness 10 preferably comprises at least one further layer. The further layer and/or layers can for example have cushioning, strengthening and/or other advantageous properties. In some embodiments, outer substance strand 20 and inner substance strand 21 can be formed with at least one further layer as a spacer knit.

Harnesses 10 can preferably have, at least in some regions, at least one cushioning layer 22 in order to increase the wearing comfort.

The cushioning layer 22 is produced, for example, from foamed material, wadding, woven fabric, cotton, wool, rubber, neoprene, gel and/or other elastic and/or viscoelastic materials.

The cushioning layer 22 has a thickness D22. The thickness D22 can be constant, for example. In alternative illustrative embodiments, the thickness D22 can also have different thicknesses in different portions of the harness 10.

The thickness D22 of the cushioning layer 22 lies, for example, in a range from about 0.5 mm to about 6 mm. Preferably, the thickness D22 of the cushioning layer 22 lies in a range from about 1.5 mm to about 3 mm.

In some embodiments, the cushioning layer 22 can be applied to the outer substance strand 20 and/or to the inner substance strand 21. When placed on the head 60, the cushioning layer 22 can then bear at least in some regions on the user's skin (not shown). In alternative embodiments, the cushioning layer 22 can also be integrated (not shown) in the substance strand 20, 21. In some embodiments, the cushioning layer 22 is arranged between the outer substance strand 20 and the inner substance strand 21 and forms at least one intermediate layer (FIGS. 5A-5C).

Harnesses 10 without forehead supports preferably have, at least in some regions, at least one strengthening layer 24 (see FIGS. 5A-5C). The strengthening layer 24 should have a certain stiffness while at the same time having flexibility, so as to give the harness 10 sufficient stability and yet still allow it to bear on the head 60.

The strengthening layer 24 can consist of strengthening elements 26 or comprise these. The strengthening elements 26 can constitute the strengthening layer 24. The strengthening elements 26 can also be integrated in a base material of the strengthening layer 24.

The strengthening layer 24 and/or the strengthening elements 26 can be applied (not shown) to the substance strand 20, 21. The strengthening layer 24 and/or the strengthening elements 26 can be integrated (not shown) in the substance strand 20, 21. In an alternative embodiment, the strengthening layer 24 and/or the strengthening elements 26 are arranged between the outer substance strand 20 and the inner substance strand 21 and form an intermediate layer (FIGS. 5A-5C).

The strengthening layer 24 and/or the strengthening elements 26 are made, for example, from plastic, metal, silicone, foamed material and/or a material composite.

The strengthening layer 24 and/or the strengthening elements 26 can be in the form of rigid plastic, wire, inorganic and/or organic reinforcement fibers, short and/or long fibers, rods, strips, woven fabric, braid, latticework and/or structural mats.

In some embodiments, the strengthening layer 24 can be designed as a deformable element that can be individually adapted to the shape of the head. For example, the strengthening layer 24 can be formed from at least one wire made of a wrought alloy, for example an aluminum wrought alloy. Other materials with deformable properties are also conceivable, for example plastics such as thermoplastics or similar.

The strengthening layer 24 and/or the strengthening elements 26 are preferably produced from a rigid plastic. The strengthening layer 24 and/or the strengthening elements 26 are produced from polypropylene, for example.

In an alternative embodiment, the strengthening layer 24 and/or the strengthening elements 26 are formed from a material composite, preferably of a rigid plastic and silicone and/or of a rigid plastic and a thermoplastic elastomer (TPE).

The strengthening layer 24 and/or the strengthening elements 26 are not limited to these embodiments. Any materials that have strengthening and/or stiffening properties are conceivable.

The further layers, for example the cushioning layer 22 and/or the strengthening layer 24, can be applied to the substance strand 20, 21 from the outside and/or integrated into the substance strand 20, 21 and/or arranged between two substance strands 20, 21. For example, at least one intermediate layer can be formed between the inner substance strand 21 and the outer substance strand 20 (see FIGS. 5A-5C).

The connection of the inner substance strand 21 to the outer substance strand 20 and/or the intermediate layers can be releasable and/or non-releasable.

The connection of the inner substance strand 21 to the outer substance strand 20 and/or the intermediate layers can be done, for example, by adhesive bonding, welding, Velcro, sewing, lamination and/or flame lamination. It is also conceivable that there is a pocket in the cushioning layer 22, into which pocket the strengthening layer 24 is introduced. The cushioning layer 22 can also have a clasp around the strengthening layer 24 and can thus be clipped onto the strengthening layer 24.

The connection between the substance strand 20, 21 and the cushioning layer can be effected by lamination, for example. In this case, the connection is produced by means of wet or dry adhesive. However, it is also possible to produce the connection without adhesive, only by heat and pressure, for example by flame lamination.

FIGS. 5A-5C show, by way of example, embodiments in which the harness 10 is designed in such a way that at least one intermediate layer is arranged between the outer substance strand 20 and the inner substance strand 21.

In the embodiment according to FIG. 5A, a strengthening layer 24 with strengthening elements 26 is arranged adjacent to the outer substance strand 20. A cushioning layer 22 is arranged adjacent to the inner substance strand 21. In this embodiment, further layers are not provided. Thus, strengthening layer 24 and cushioning layer 22 are arranged next to each other and together form the intermediate layer, which is arranged between the outer substance strand 20 and the inner substance strand 21.

In the embodiment according to FIG. 5B, a first cushioning layer 22 is arranged adjacent to the outer substance strand 20. A second cushioning layer 22 is arranged adjacent to the inner substance strand 21. The strengthening layer 24 with strengthening elements 26 is arranged between the two cushioning layers 22. In this embodiment, further layers are not provided.

Thus, the strengthening layer 24 is arranged between two cushioning layers 22. The strengthening layer 24 and the two cushioning layers 22 together form the intermediate layer, which is arranged between the outer substance strand 20 and the inner substance strand 21.

In the embodiment according to FIG. 5C, a cushioning layer 22 is arranged between the outer substance strand 20 and the inner substance strand 21, in which cushioning layer 22 the strengthening elements 26 are integrated. Thus, the cushioning layer 22 is also designed as strengthening layer 24. Accordingly, between the outer substance strand 20 and the inner substance strand 21, an intermediate layer is formed which at the same time has strengthening and cushioning properties.

The specially shaped temple portion 36 can be designed on the basis of all of the illustrative embodiments shown in FIGS. 5A-5C. The invention is not limited to the illustrative embodiments shown in FIGS. 5A-5C. The harness 10 according to the invention expressly also includes harnesses 10 whose general structure is not shown in FIGS. 5A-5C, for example harnesses 10 in which the cushioning layer 22 and/or the strengthening layer 24 are applied to the outer substance strand 20 and/or the inner substance strand 21 and/or are integrated in the substance strand 20, 21.

FIGS. 6A, 6B, 7A, 7B, 8A, 8B, 9, 10A and 10B show different illustrative embodiments of the temple portion 36 of the harness 10 in cross section. According to the invention, the harness 10 has, at least in some regions, an eyeglass tunnel 40, which is configured and designed to at least partially receive at least one eyeglass arm 64.

As is explained on the basis of the following illustrative embodiments, the eyeglass tunnel 40 can be reversible and/or irreversible.

Figure 9:
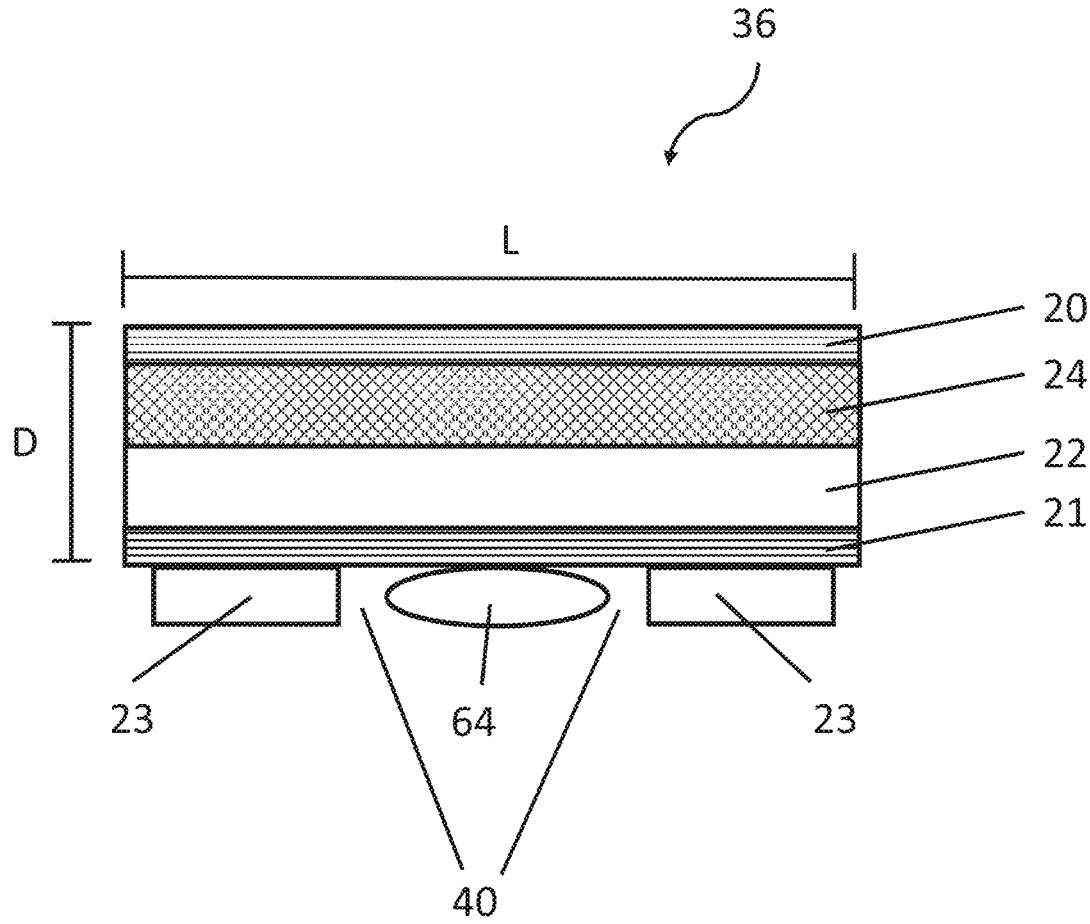

A reversible eyeglass tunnel 40 is obtained here by the action of the eyeglass arm 64 (see FIGS. 6A, 6B, 7A, 7B) and/or by a releasable add-on to the harness 10 (see FIG. 9).

By contrast, an irreversible eyeglass tunnel 40 is obtained by a non-releasable add-on to the harness 10 (see FIG. 9) and/or by an at least partial cutout in the inner substance strand 21 and/or in the strengthening layer 24 and/or in the cushioning layer 22 and/or in the outer substance strand 20 (see FIG. 8) and/or by an at least regional and/or at least partial deformation of the harness 10 (see FIG. 10).

Figure 6A:
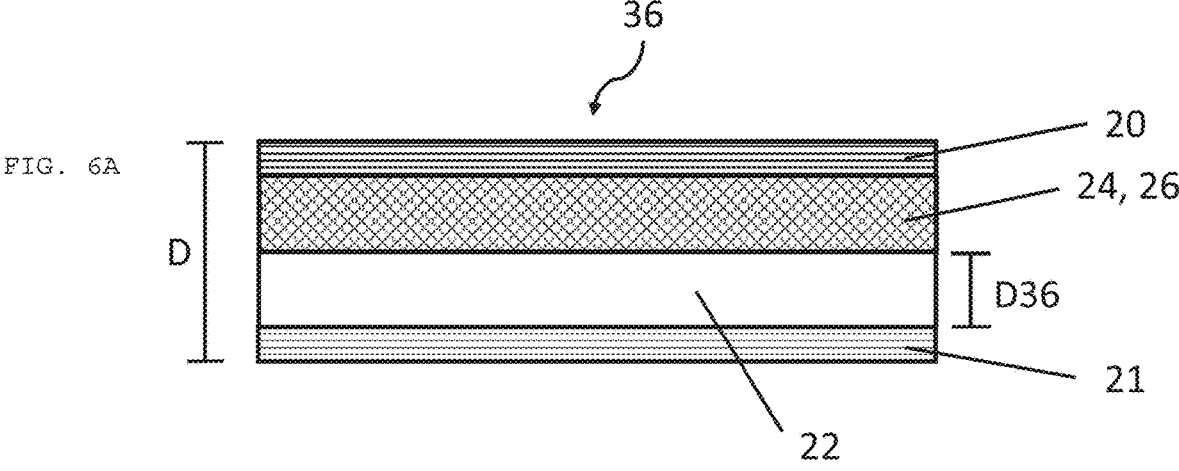
FIGS. 6A, 6B, 7A, 7B, 8A, 8B, 9, 10A and 10B show different illustrative embodiments of the temple portion, according to the invention, of the harness in cross section.
Figure 6B:
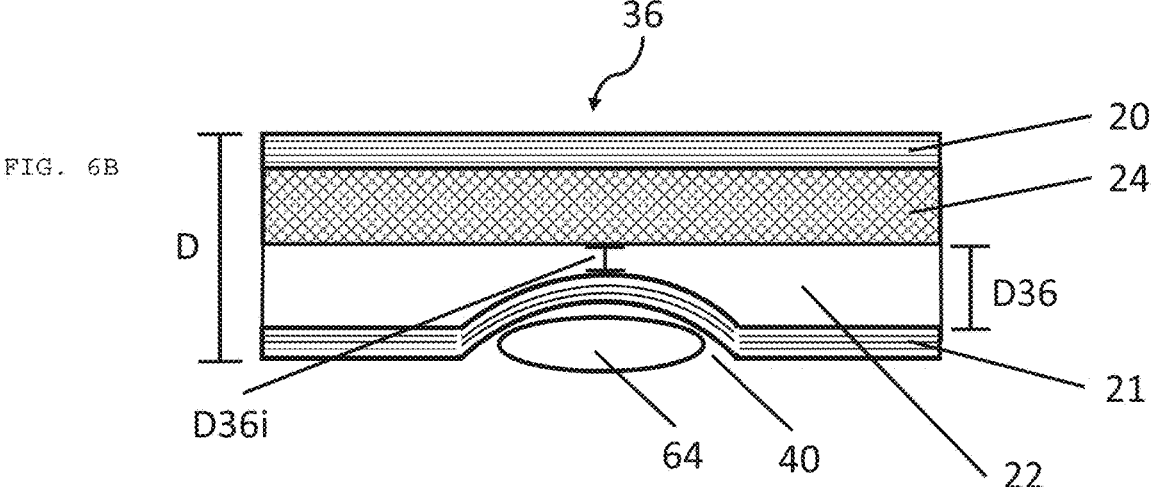

FIGS. 6A and 6B show an embodiment for the temple portion 36 in cross section. It is clear from FIGS. 6A and 6B that the general structure can correspond to the structure of the harness 10 shown in FIG. 5A. In other embodiments, the general structure can also correspond to the structure shown in FIGS. 5B and/or 5C, or it can be such that the cushioning layer 22 and/or the strengthening layer 24 are/is applied to and/or integrated in the substance strand 20, 21 (not shown).

It is clear from FIGS. 6A and 6B that the cushioning layer 22 in the temple portion 36 has a thickness D36. The thickness D36 can correspond to the thickness D22 of the cushioning layer 22 of the other portions of the harness 10. The thickness D22/D36 of the cushioning layer 22 can accordingly be constant.

In this illustrative embodiment, the cushioning layer 22 and/or the strengthening layer 24 and/or the substance strand 20, 21 have a material weakening at least in some regions.

In an illustrative embodiment, the cushioning layer 22 in the temple portion 36 is softer than in the other portions of the harness 10 (FIG. 6A). In this context, "softer" means that less force has to be applied to compress the cushioning layer 22 in the temple portion 36 than is needed to compress the cushioning layer 22 in other portions of the harness 10.

For example, the force needed to compress the cushioning layer 22 by 25% to the thickness D36i (see FIG. 6B) in the temple portion 36 is at least about 10% less, preferably at least about 20% less, particularly preferably about 30% less than in the other portions of the harness. The degree of hardness of the cushioning material in the temple portion 36 is accordingly less than in the other portions of the harness 10.

The degree of hardness of the cushioning material in the temple portion 36 is chosen such that an eyeglass arm 64 (not shown), which extends under the temple portion 36, slightly displaces the cushioning material in such a way that there is no unpleasant pressure of the eyeglass arm 64 on the head 60 of the user.

If an eyeglass arm 64 extending under the temple portion 36 displaces the cushioning layer 22 to the thickness D36i, an eyeglass tunnel 40 forms. The eyeglass tunnel 40 is created by the pressure that an eyeglass arm 64 exerts on the head 60 of the user.

In this embodiment, the eyeglass tunnel 40 forms reversibly, as soon as an eyeglass arm 64 is located under the temple portion 36. When the eyeglass arm 64 is removed, the cushioning layer 22 widens again to its original thickness D36 and the eyeglass tunnel 40 disappears.

The cushioning layer 22 of the harness 10 can be made of one material or of at least two different materials.

In some embodiments, provision is made that the cushioning layer 22 in the temple portion 36 is produced from a different material than the cushioning layer 22 in the other portions of the harness 10, in order to obtain softer cushioning in the temple portion 36 than in the rest of the harness 10.

In other embodiments, the material of the cushioning layer 22 in the temple portion 36 is the same as in the other portions of the harness 10, but it has other material properties at least in some regions. For example, the cushioning layer 22 in the temple portion 36 can have a differing material density and/or another chemical makeup. For example, the chemical makeup can differ in respect of the molecular chain length, the number of crosslinks within the molecular chain, the structure of the molecular chains and similar, such that the material of the cushioning layer 22 in the temple portion is softer than in the other portions of the harness 10.

In embodiments in which the cushioning layer 22 is made of foamed material, the foamed material can, for example, have different pore numbers and/or pore sizes, such that the cushioning layer 22 in the temple portion 36 is softer than in the other portions of the harness 10.

A further cushioning layer 22 in the temple portion 36 is also possible for the general structure of the embodiments according to FIGS. 5B and/or 5C.

As regards the structure according to FIG. 5C, this can mean that the one intermediate layer, which simultaneously has strengthening and cushioning properties, has a weakening in the temple portion 36. For example, the intermediate layer in the temple portion 36 cam have fewer and/or no strengthening properties (not shown).

Figure 7A:
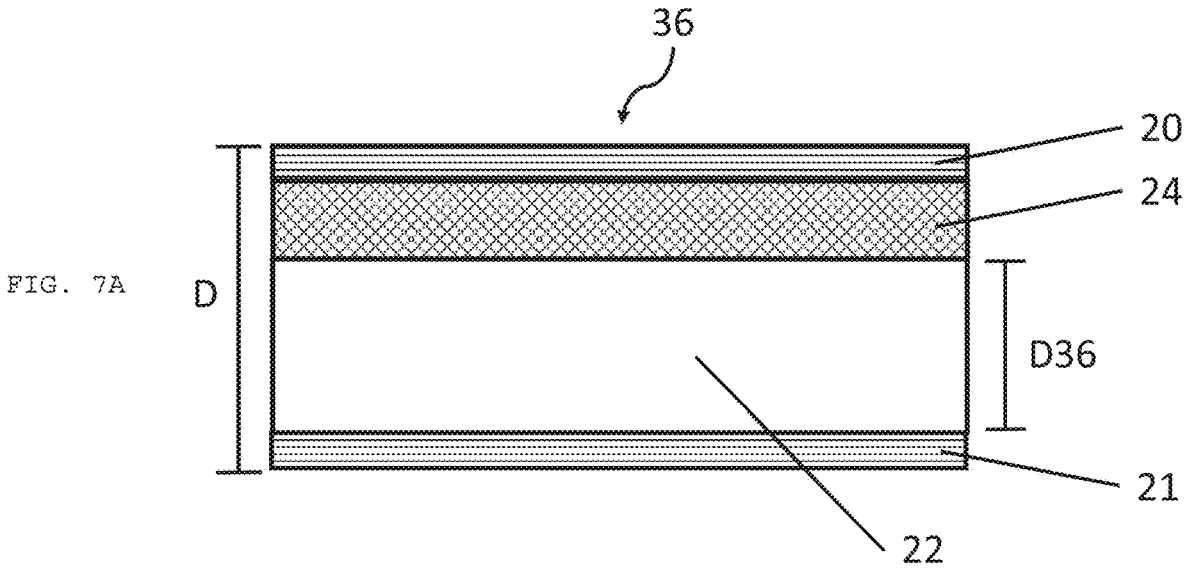
Figure 7B:
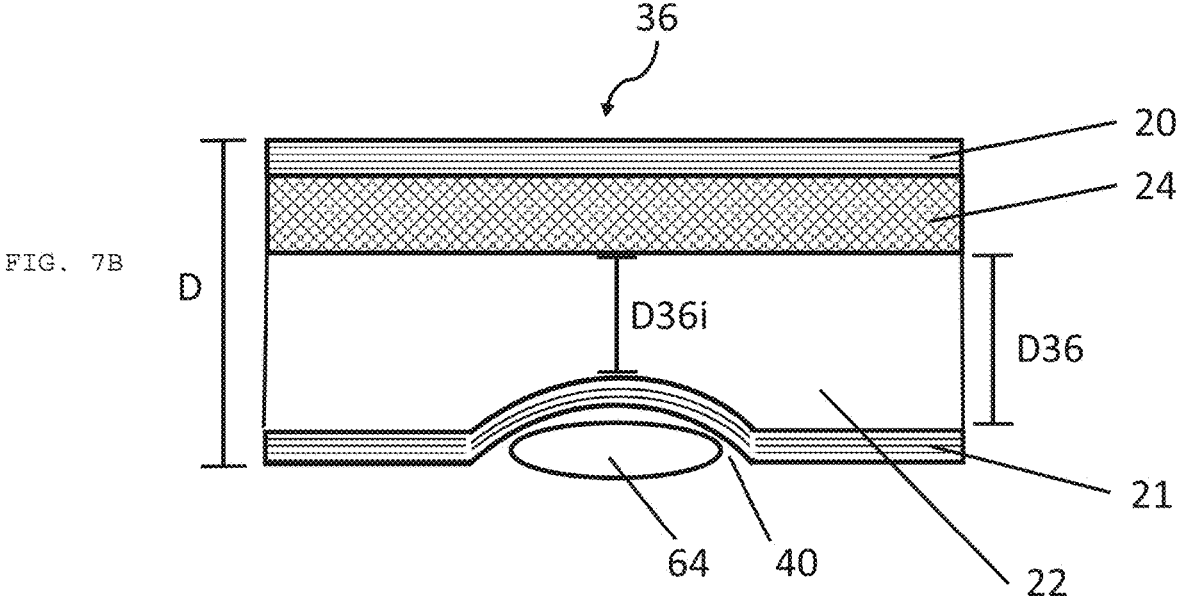

FIGS. 7A and 7B show an alternative embodiment of the temple portion 36 in cross section. It is clear from FIGS. 7A and 7B that the general structure can correspond to the structure of the harness 10 shown in FIG. 5A. In other embodiments, the general structure can also correspond to the structure shown in FIGS. 5B and/or 5C, or it can be such that the cushioning layer 22 and/or the strengthening layer 24 are/is applied to and/or integrated in the substance strand 20, 21 (not shown).

However, it is clear from FIG. 7A that, in this embodiment, the cushioning layer 22 in the region of the temple portion 36 has a greater thickness than in the portions of the harness 10 that are not located in the temple portion 36 (D22, cf. FIG. 5A).

The thickness D36 of the cushioning layer 22 in the temple portion 36 can, for example, be at least about 1 mm thicker than the thickness D22 in the other portions of the harness 10. Preferably, the thickness D36 of the cushioning layer 22 in the temple portion 36 is at least about 3 mm thicker than the thickness D22 in the other portions of the harness 10. For example, the thickness D22 of the cushioning layer 22 of the harness 10 is generally from about 1.5 mm to about 3 mm thick and increases in the temple portion 36 to a thickness D36 of from about 4.5 mm to about 6 mm.

The thickness D36 of the cushioning layer 22 can increase abruptly in the temple portion 36. In an alternative embodiment, the thickness D36 of the cushioning layer 22 can also increase successively, in such a way that the cushioning layer 22 in the temple portion has the thickness D36 and is constant there (not shown).

The thickness D36 is chosen in such a way that an eyeglass arm 64 (not shown), which extends under the temple portion 36, displaces the cushioning layer 22 in such a way that the cushioning layer 22 has a thickness D36*i* in the region (see FIG. 7B). The thickness D36*i* is less than the thickness D36.

If an eyeglass arm 64 extending under the temple portion 36 displaces the cushioning layer 22 to the thickness D36*i*, the eyeglass tunnel 40 forms.

The eyeglass tunnel 40 is created by the pressure that an eyeglass arm 64 exerts on the cushioning layer 22.

In this embodiment, the eyeglass tunnel 40 is formed reversibly. When the eyeglass arm 64 is removed from the temple portion 36, the cushioning layer 22 can widen again in the region to the original thickness D36.

A thicker cushioning layer 22 in the temple portion 36 is also possible for other harnesses 10, for example corresponding to the embodiment according to FIGS. 5B and/or 5C.

Figure 8A:
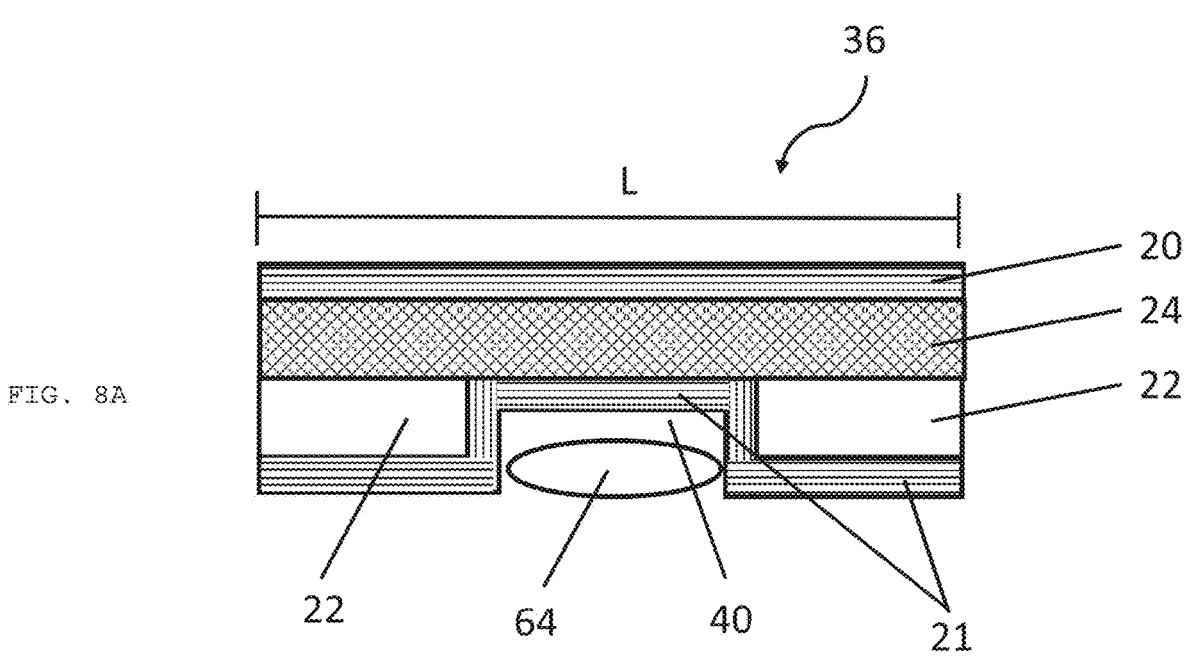
Figure 8B:
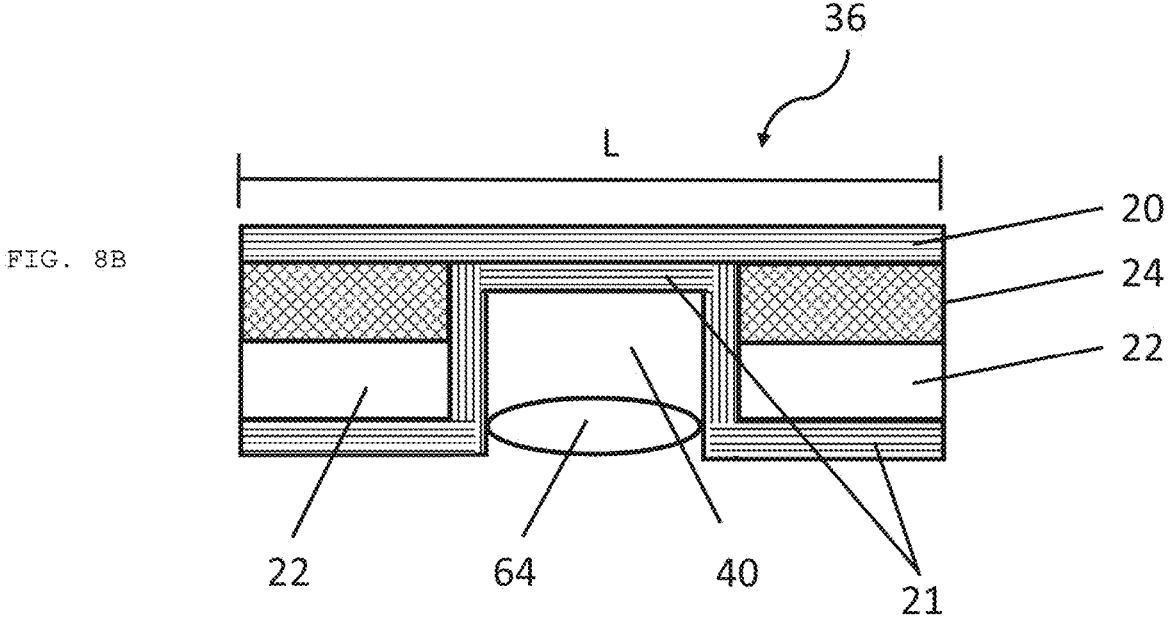

FIGS. 8A and 8B show an alternative embodiment of the temple portion 36 in cross section. It is clear from FIGS. 8A and 8B that the general structure can correspond to the structure of the harness 10 shown in FIG. 5A. In other embodiments, the general structure can also correspond to the structure shown in FIGS. 5B and/or 5C, or it can be such that the cushioning layer 22 and/or the strengthening layer 24 are/is applied to and/or integrated in the substance strand 20, 21 (not shown).

It is clear from FIGS. 8A and 8B that the harness 10 in this embodiment has at least one cutout. The cutout can be formed at least in part in the cushioning layer 22 and/or in the strengthening layer 24 and/or in the substance strand 20, 21. Thus, in some embodiments, the cushioning layer 22 and/or the strengthening layer 24 and/or the substance strand 20, 21 can be thinner in the temple portion 36 than in the other portions of the harness 10 (not shown).

In an alternative embodiment, the cutout can involve the whole cushioning layer 22 and/or the strengthening layer 24 and/or the substance strand 20, 21. For example, the cushioning layer 22 and/or the strengthening layer 24 in the region of the temple portion 36 can have a cutout (see FIGS. 8A and 8B). This means that the cushioning layer 22 and/or the strengthening layer 24 do not extend over the full length L of the temple portion 36.

The cutout can comprise a total of about 20% to about 100% of the length L of the temple portion 36, preferably from about 50% to about 100%. For example, the cutout comprises about 80% of the length L of the temple portion 36.

In one embodiment, the eyeglass tunnel 40 is formed by the cutout in the cushioning layer 22 (FIG. 8A). Alternatively or in addition, the strengthening layer 24 can also have a corresponding cutout (FIG. 8B). The eyeglass tunnel 40 in this illustrative embodiment is pre-shaped and irreversible.

The eyeglass tunnel 40 formed by the cutout can be from about 3 mm to about 30 mm high. Preferably, the eyeglass tunnel 40 is from about 5 mm to about 20 mm high.

In the region of the eyeglass tunnel 40, the inner substance strand 21 can be connected directly to the strengthening layer 24. The eyeglass tunnel 40 can then be delimited by the inner substance strand 21 (see FIG. 8A). The inner substance strand 21 can also be connected directly to the outer substance strand 20. The eyeglass tunnel 40 can then be delimited by the inner substance strand 21 (see FIG. 8B).

It is also conceivable that the inner substance strand 21 in the region of the eyeglass tunnel 40 also has a cutout corresponding to the cushioning layer 22 and/or the strengthening layer 24 (not shown). Then, the temple portion 36 in the region of the eyeglass tunnel 40 would exclusively comprise the strengthening layer 24 and/or the outer substance strand 20.

In this embodiment, the eyeglass tunnel 40 extends for example over about 20% to about 100% of the length L of the temple portion 36, preferably over about 50% to about100%. For example, the eyeglass tunnel 40 extends over 80% of the length L of the temple portion 36.

The eyeglass tunnel 40 is designed and configured such that the user is able to guide an eyeglass arm 64 in through the eyeglass tunnel 40 and/or out through the eyeglass tunnel, thus allowing a patient interface 90 with harness 10 to be used at the same time as eyeglasses.

FIG. 9 shows an alternative embodiment of the temple portion 36 in cross section. It is clear from FIG. 9 that the general structure can correspond to the structure of the harness 10 shown in FIG. 5A. In other embodiments, the general structure can also correspond to the structure shown in FIGS. 5B and/or 5C, or it can be such that the cushioning layer 22 and/or the strengthening layer 24 are/is applied to and/or integrated in the substance strand 20, 21 (not shown).

In this illustrative embodiment, provision is made that one or more spacer cushions are arranged in the temple portion 36.

In a simple embodiment, the temple portion 36 comprises one spacer cushion 23, which is arranged in the temple portion 36 in such a way that, after the harness has been placed on the head 60, a gap is created between harness 10 and head 60, through which gap an eyeglass arm 64 can be guided (not shown).

In a preferred embodiment, the temple portion 36 comprises two spacer cushions 23. The, for example, two spacer cushions 23 can be arranged spaced apart from each other in such a way that the eyeglass tunnel 40 is obtained (see FIG. 9).

The eyeglass tunnel 40 can be pre-shaped by the spacer cushions 23.

The spacer cushions 23 can for example be made of the same material as the cushioning layer 22. The spacer cushions 23 can also be made of a different material than the cushioning layer 22, a material which appears suitable in terms of biocompatibility and comfort.

The spacer cushions 23 can for example have the same thickness as the cushioning layer 22. The spacer cushions 23 can also be thicker or thinner than the cushioning layer 22. For example, the eyeglass tunnel 40 can be made from about 3 mm to about 30 mm high by the spacer cushions 23. Preferably, the eyeglass tunnel 40 is from about 5 mm to about 20 mm high.

The spacer cushions 23 can be integrally formed on the inner substance strand 21. However, in alternative embodiments, the spacer cushions 23 can also be arranged inside the substance strand 20, 21, for example between the inner substance strand 21 and the cushioning layer 22 (not shown).

The spacer cushions 23 are connected to the harness 10 at least in some regions. The spacer cushions are preferably connected to the temple portion 36 at least in some regions.

In some embodiments, the spacer cushions 23 can be arranged only on one side of the harness 10. For example, the spacer cushions 23 are arranged in such a way that, after being placed on the head 60 of the user (not shown), they are located between harness 10 and head 60. In this case, the spacer cushions 23 can be arranged for example on the inner substance strand 21 (see FIG. 9).

In an alternative illustrative embodiment, provision is made that the at least one spacer cushion 23 in the temple portion 36 is arranged in an annular shape (not shown) around the harness 10.

The spacer cushions 23 can be connected fixedly and irreversibly to the temple portion 36. For example, the spacer cushions 23 can be adhesively bonded, sewn, stitched, welded, stapled or the like onto regions of the temple portion 36.

In a particularly advantageous embodiment, the spacer cushions 23 can also be connected reversibly to the temple portion 36. For example, it is conceivable that the spacer cushions 23 are connected to the temple portion 36 via a hook-and-loop fastener or another reversible connection. A further possibility is afforded by annular spacer cushions 23. These can be pushed onto the harness 10 by the user, when so required, and positioned in the temple portion 36. A reversible connection affords the user the advantage of individual adaptation to his or her requirements. In this way, the user can adapt the eyeglass tunnel 40 to the eyeglasses that are being used. Moreover, the user is able to create the eyeglass tunnel 40 only when eyeglasses are being used.

The spacer cushions 23 are in total arranged for example over about 20% to about 80% of the length L of the temple portion 36, preferably over about 40% to about 70%. For example, the spacer cushions 23 are in total arranged over about 50% of the length L of the temple portion 36.

In this embodiment, the eyeglass tunnel 40 formed by the spacer cushions 23 extends for example over about 80% to about 20% of the length L of the temple portion 36, preferably over about 60% to about 30%. For example, the eyeglass tunnel 40 extends over about 50% of the length L of the temple portion 36.

Figure 10A:
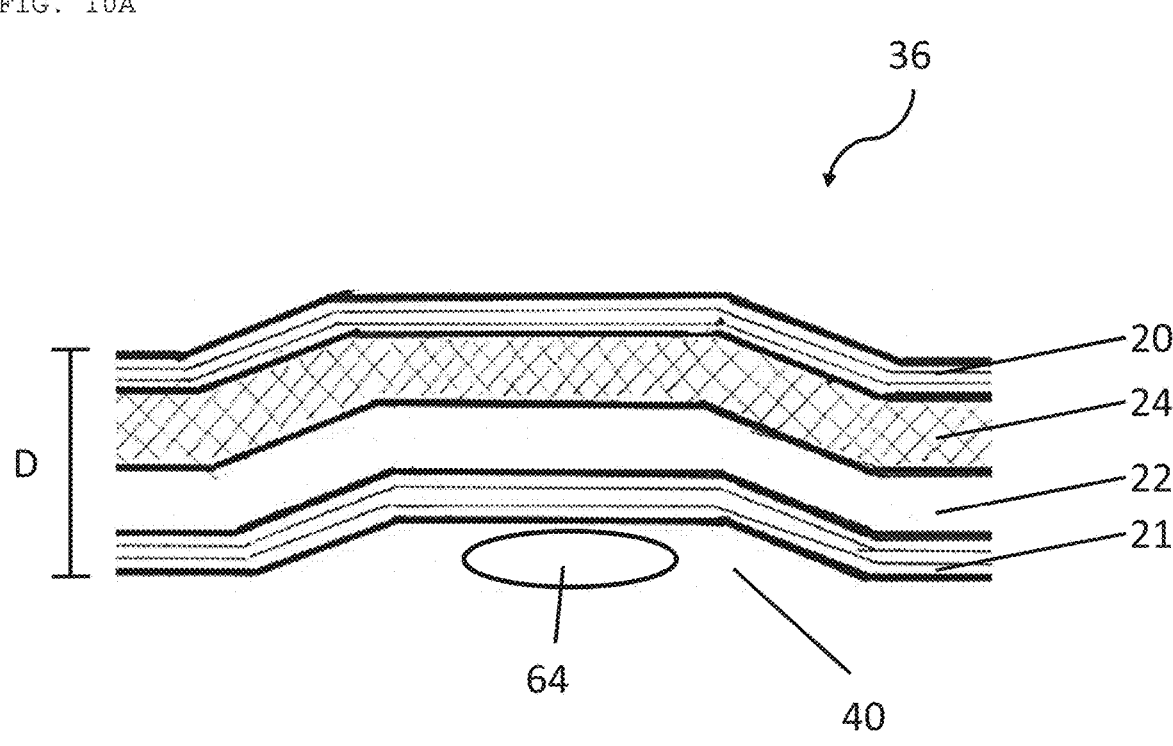
Figure 10B:
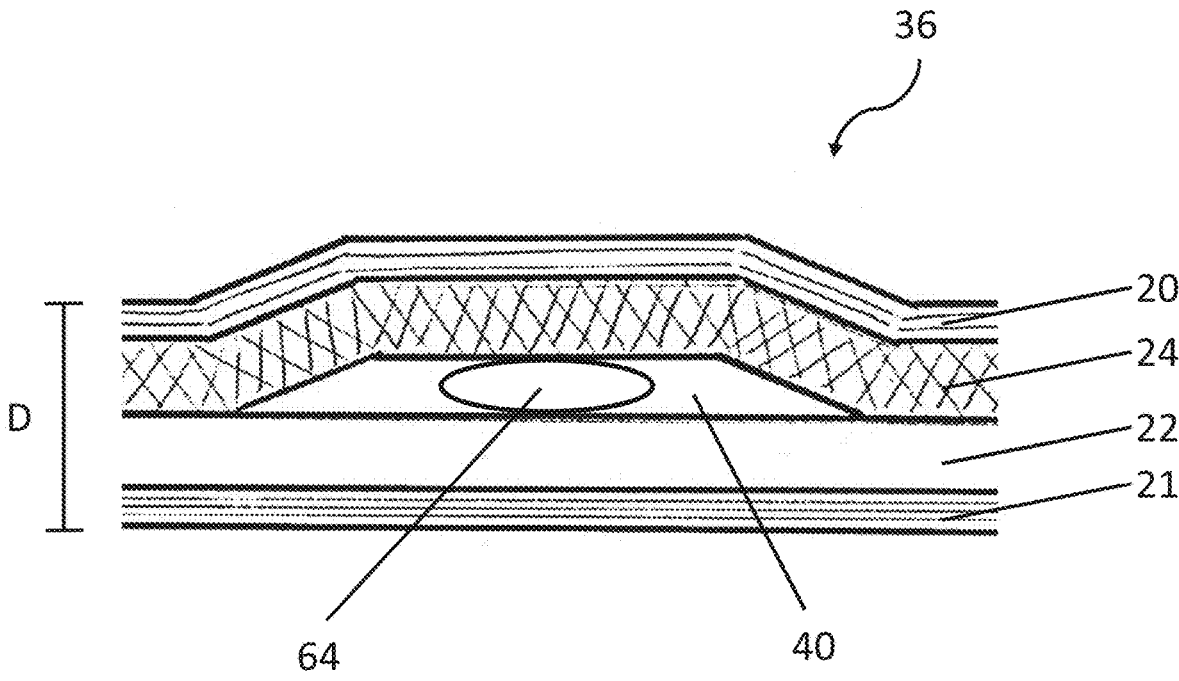

FIGS. 10A and 10B show an alternative embodiment of the temple portion 36 in cross section.

It is clear from FIGS. 10A and 10B that the general structure can correspond to the structure of the harness 10 shown in FIG. 5A. In other embodiments, the general structure can also correspond to the structure shown in FIGS. 5B and/or 5C, or it can be such that the cushioning layer 22 and/or the strengthening layer 24 are/is applied to and/or integrated in the substance strand 20, 21 (not shown).

In this embodiment, provision is made that the temple portion 36, at least in some regions, has an at least partial pre-shaped contour for forming the eyeglass tunnel 40. In this context, "pre-shaped contour" means that at least parts of the harness 10 are pre-shaped at least in some regions. The harness 10 is elastically deformable only to a limited extent in this region and does not lose its pre-shaped contour even under tensile force.

All of the layers of the harness 10 can have a pre-shaped contour in at least some regions in the temple portion 36, or just individual layers. All possible combinations are conceivable.

In this embodiment, the harness 10 is in particular pre-shaped in such a way that a curvature is formed which constitutes the eyeglass tunnel 40. For example, the harness 10 can be designed in such a way that the eyeglass tunnel 40 is formed between the harness 10 and the head 60 (not shown) of the user (see FIG. 10A) and/or inside the harness 10 (see FIG. 10B).

FIG. 10A shows an illustrative embodiment. All the layers of the harness 10 have a pre-shaped contour in the region of the temple portion 36. The eyeglass tunnel 40 is at least partially delimited by the inner substance strand 21. After the harness 10 has been placed on the head 60, the eyeglass tunnel 40 is located between the inner substance strand 21 and the head 60 (not shown) of the user. An eyeglass arm 64 can then be received in the eyeglass tunnel 40.

When placed on the head 60 of the user, the harness 10 can in at least some regions cross the straight lines G1 and G2 shown in FIG. 2.

In the illustrative embodiment according to FIG. 10A, the above-described curvature, which forms the eyeglass tunnel 40, is arranged according to the invention between the inner substance strand 21 of the harness 10 and a straight line (not shown) drawn between the intersection points.

In some embodiments, the harness 10 can have no inner substance strand 21, such that the curvature, which forms the eyeglass tunnel 40, can also extend between the cushioning layer 22 and the straight lines drawn between the intersection points. In an alternative embodiment, the harness 10 can have neither the inner substance strand 21 nor the cushioning layer 22, such that the curvature, which forms the eyeglass tunnel 40, can also extend between the strengthening layer 24 and the straight lines drawn between the intersection points.

The curvature measures at least about 3 mm. The pre-shaped contour is configured and designed in such a way that the eyeglass tunnel 40 is from about 3 mm to about 30 mm high, preferably from about 5 mm to about 20 mm high.

In alternative illustrative embodiments, individual layers and/or multiple layers of the harness 10 can have a pre-shaped contour in the temple portion 36, while other layers have no specially pre-shaped contour.

FIG. 10B shows an illustrative embodiment in which only the strengthening layer 24 and the outer substance strand 20 have a pre-shaped contour. In this illustrative embodiment, the cushioning layer 22 and the inner substance strand 21 are designed without a pre-shaped contour.

When placed on the head 60 of the user, the harness 10 can in at least some regions cross the straight lines G1 and G2 shown in FIG. 2.

In this embodiment, the above-described curvature, which forms the eyeglass tunnel 40, is arranged according to the invention between the strengthening layer 24 and the straight line (not shown) drawn between the intersection points. The curvature measures at least about 3 mm. The pre-shaped contour is designed and configured in such a way that the eyeglass tunnel 40 is from about 3 mm to about 30 mm high, preferably from about 5 mm to about 20 mm high.

Since the cushioning layer 22 and the inner substance strand 21 in this illustrative embodiment have no pre-shaped contour, the cushioning layer 22 and the inner substance strand lie on a plane with the straight line drawn between the intersection points. The gap, which constitutes the eyeglass tunnel 40, is thus formed between the strengthening layer 24 and the cushioning layer 22. Thus, strengthening layer 24 and cushioning layer 22 are arranged spaced apart from each other in such a way that the eyeglass tunnel 40 is formed. The eyeglass tunnel 40 is from about 3 mm to about 30 mm high, preferably from about 5 mm to about 20 mm high.

In an alternative illustrative embodiment, the strengthening layer 24 and the cushioning layer 22 and the outer substance strand 20 can have a pre-shaped contour. In this case, a gap, which constitutes the eyeglass tunnel 40 (not shown), is formed between the cushioning layer 22 and the inner substance strand 21.

In relation to the structure according to FIG. 5C, the pre-shaped contour according to the invention can mean that the intermediate layer, which has strengthening and cushioning properties simultaneously, and/or the substance strand 20, 21 in the temple portion 36 has a pre-shaped contour, such that the eyeglass tunnel 40 is formed (not shown).

To sum up, the present invention provides:

1. A harness for a patient interface, wherein the harness comprises, at least in some regions, an eyeglass tunnel which is configured and designed to at least partially receive at least one eyeglass arm.

2. The harness of item 1, wherein the harness comprises a temple portion, which at least in some regions comprises the at least one eyeglass tunnel, the temple portion being the portion of the harness which, after being placed on a head of a user, extends over a temple region of the head.

3. The harness of at least one of the preceding items, wherein the harness comprises an inner fabric strand and/or a strengthening layer and/or a cushioning layer and/or an outer fabric strand.

4. The harness of at least one of the preceding items, wherein the eyeglass tunnel is reversible and/or irreversible.

5. The harness of item 4, wherein the reversible eyeglass tunnel is formed by the action of the eyeglass arm and/or by a releasable add-on to the harness.

6. The harness of item 4 or item 5, wherein the irreversible eyeglass tunnel is formed by a non-releasable add-on to the harness and/or by an at least partial cutout in an inner fabric strand and/or in a strengthening layer and/or in a cushioning layer and/or in an outer fabric strand and/or by an at least partial pre-shaping, at least in some regions, of the harness.

7. The harness of at least one of the preceding items, wherein a material weakening is formed at least in some regions in a cushioning layer and/or in a strengthening layer and/or in a fabric strand of the temple portion, the weakening being designed and configured in such a way that the eyeglass tunnel is formed reversibly at least in some regions in the temple portion by the action of the eyeglass arm.

8. The harness of item 7, wherein the weakening is formed by an at least regionally lower degree of hardness of a material of the cushioning layer and/or of the strengthening layer and/or of the fabric strand.

9. The harness of at least one of the preceding items, wherein the cushioning layer has a thickness which is constant, or which in at least some regions is not constant.

10. The harness of at least one of the preceding items, wherein a cushioning layer has a substantially constant thickness and in a temple portion has a thickness which is at least regionally greater than a thickness of the cushioning layer, the material of the cushioning layer being displaced by an action of the eyeglass arm in such a way that the eyeglass tunnel is reversible.

11. The harness of at least one of the preceding items, wherein the harness comprises at least one spacer cushion, which is connected releasably and/or non-releasably to the harness.

12. The harness of item 11, wherein the spacer cushion is connected at least in some regions to the harness, preferably at least in some regions to the temple portion, the spacer cushion being arranged in the temple portion in such a way that the eyeglass tunnel is reversible and/or irreversible.

13. The harness of item 12, wherein the spacer cushion is fastened to the harness and/or is integrated in the harness.

14. The harness of at least one of the preceding items, wherein the eyeglass tunnel is formed by an at least partial cutout in a cushioning layer and/or in a strengthening layer and/or in a fabric strand.

15. The harness of at least one of the preceding items, wherein the eyeglass tunnel is formed by an at least partial cutout of a cushioning layer and/or of a strengthening layer and/or of a fabric strand.

16. The harness of at least one of the preceding items, wherein the temple portion has a length L, and a cutout in a cushioning layer and/or in a strengthening layer and/or in a fabric strand and/or a cutout of a cushioning layer and/or of a strengthening layer and/or of a fabric strand comprises from 20% to 100% of the length L of the temple portion, preferably from 50% to 100%, particularly preferably 80% of the length L of the temple portion.

17. The harness of at least one of the preceding items, wherein the harness comprises, at least in some regions, an at least partial pre-shaped contour which irreversibly forms the eyeglass tunnel.

18. The harness of at least one of the preceding items, wherein an inner fabric strand and/or a cushioning layer and/or a strengthening layer and/or an outer fabric strand have a pre-shaped contour in a temple portion.

19. The harness of at least one of the preceding items, wherein the harness is pre-shaped in a temple portion in such a way that the harness, after being placed on a head of a user, is at least partially spaced apart from the head of the user, so that the eyeglass tunnel is formed.

20. The harness of at least one of the preceding items, wherein an inner fabric strand and a cushioning layer do not have a pre-shaped contour in a temple portion, and a strengthening layer and/or an outer fabric strand do have a pre-shaped contour, in such a way that cushioning layer and strengthening layer are spaced apart from each other and form the eyeglass tunnel.

21. The harness of at least one of the preceding items, wherein the eyeglass tunnel is from 3 mm to 30 mm high, preferably from 5 mm to 20 mm high.

LIST OF REFERENCE SIGNS 10 harness
20 outer substance strand
21 inner substance strand
22 cushioning layer
23 spacer cushion
24 strengthening layer
26 strengthening element
30 side portion
32 second side portion
34 base portion
36 temple portion
40 eyeglass tunnel
60 head
62 temple region
64 eyeglass arm
70 ventilator
80 line
90 patient interface/respiratory mask
92 attachment point
94 second attachment point
100 system
B width
D thickness
D22 thickness of the cushioning layer
D36/D36*i* thickness of the cushioning layer in the temple portion
G1 straight line 1
G2 straight line 2
L length
pra point of the base of the ear (lat. Praeaurale)
sa highest point of the auricle (lat. Supeaurale)
sci highest point of the upper margin of the brow (lat. Superciliare)
sn subnasal point (lat. Subnasale)

What is claimed is:

1. A harness which is suitable and configured for securing a device for facilitating ventilation or respiratory assistance, or a protective mask against aerosols to a head of a user, wherein the harness comprises, at least in some regions, an eyeglass tunnel which is configured to at least partially receive at least one eyeglass arm, wherein the harness further comprises an inner fabric strand, a reinforcing layer, a cushioning layer and an outer fabric strand, and comprises a temple portion, which at least in some regions thereof comprises the at least one eyeglass tunnel, the temple portion being that portion of the harness which is configured, after being placed on the head of the user, to extend over a temple region of the head, and wherein the reinforcing layer and/or the outer fabric strand have a pre-shaped contour such that the cushioning layer and the reinforcing layer are spaced apart from one another and form the eyeglass tunnel, and the inner fabric strand and the cushioning layer do not have a pre-shaped contour in the temple portion.

2. The harness of claim 1, wherein the eyeglass tunnel is formed reversibly.

3. The harness of claim 1, wherein the eyeglass tunnel is formed irreversibly.

4. The harness of claim 1, wherein a material weakening is formed at least in some regions in the cushioning layer and/or in the reinforcing layer and/or in the inner and/or outer fabric strand of the temple portion, the material weakening being configured in such a way that the eyeglass tunnel is formed reversibly at least in some regions in the temple portion by a removal of the eyeglass arm from the temple portion.

5. The harness of claim 4, wherein the material weakening is formed by an at least regionally lower degree of hardness of a material of the cushioning layer and/or of the reinforcing layer and/or of the inner or outer fabric strand.

6. The harness of claim 1, wherein the cushioning layer has a thickness which is constant.

7. The harness of claim 1, wherein the cushioning layer has a thickness which in at least some regions is not constant.

8. The harness of claim 1, wherein in the temple portion the cushioning layer has a substantially constant thickness.

9. The harness of claim 1, wherein the harness comprises at least one spacer cushion, which is connected releasably or non-releasably to the harness.

10. The harness of claim 9, wherein the spacer cushion is connected at least in some regions to the harness and is arranged in the temple portion.

11. The harness of claim 1, wherein the temple portion has a length L, and a cutout in the cushioning layer and/or in the reinforcing layer and/or in the inner and/or outer fabric strand comprises from 20% to 100% of the length L of the temple portion.

12. The harness of claim 1, wherein the eyeglass tunnel is from 3 mm to 30 mm high.

13. The harness of claim 1, wherein the eyeglass tunnel is from 5 mm to 20 mm high.

14. The harness of claim 1, wherein the cushioning layer is formed from one or more of foamed materials, wadding, woven fabric, cotton, wool, rubber, neoprene, gel, elastic materials or viscoelastic materials.

15. The harness of claim 1, wherein the cushioning layer has a thickness ranging from 0.5 mm to 6 mm.

16. The harness of claim 1, wherein the cushioning layer has a thickness ranging from 1.5 mm to 3 mm.

* * * * *